Figure 1A:
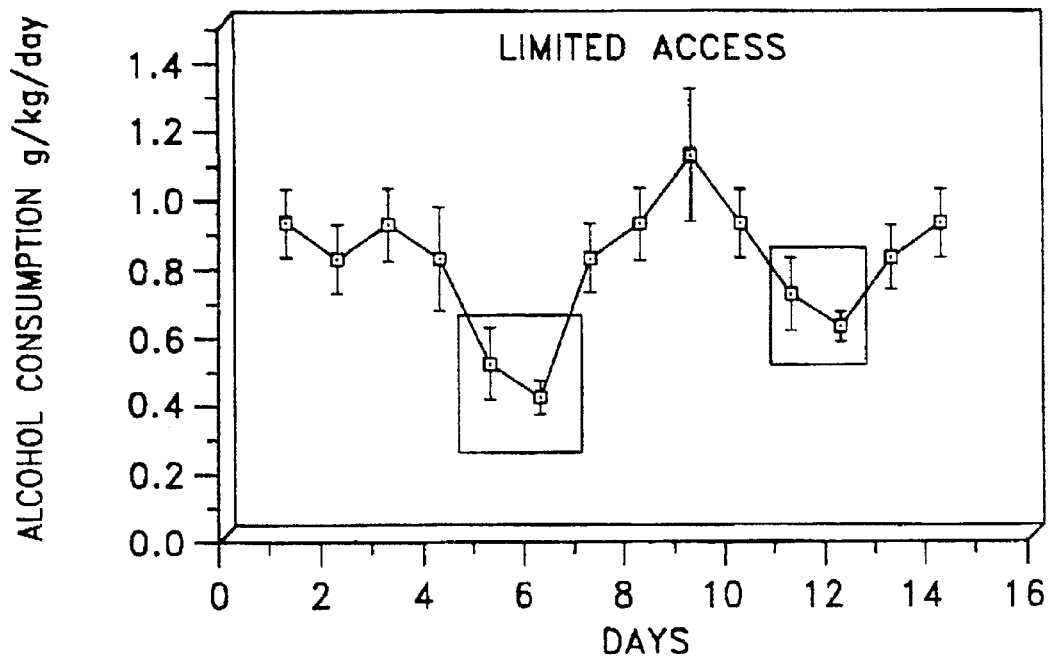

United States Patent [19]
Beauge

[11] Patent Number: 5,639,792
[45] Date of Patent: Jun. 17, 1997

[54] NO SYNTHETASE INHIBITORS AS MEDICINAL PRODUCTS INTENDED TO REDUCE ALCOHOL CONSUMPTION OR TO PREVENT EXCESSIVE ALCOHOL CONSUMPTION

[76] Inventor: Françoise Beauge, Appt. 2802 —14 Villa d'Este, 75013 Paris, France

[21] Appl. No.: 507,815

[22] Filed: Jul. 27, 1995

[30] Foreign Application Priority Data

Jul. 29, 1994 [FR] France .................................. 94 09445

[51] Int. Cl.$^6$ ................................................. A61K 31/195
[52] U.S. Cl. ............................................................. 514/565
[58] Field of Search ..................................... 514/564, 565

[56] References Cited

FOREIGN PATENT DOCUMENTS

WO93/05775  4/1993  WIPO .

OTHER PUBLICATIONS

Adams et al., *Alcoholism: Clinical and Experimental Research*, vol. 19, pp. 195–199 (1995).
Rezvani et al., *Pharmacology Biochemistry and Behavior*, vol. 50: pp. 265–270 (1995).
Khanna et al., *Brain Research Bulletin*, vol. 32, pp. 43–47 (1993).
Kolesnikov et al., *European Journal of Pharmacology*, 221: 399–400 (1992).
Hunt et al., *J. Hepalol.*, 14: 146–150 (1992).

*Primary Examiner*—Phyllis G. Spivack
*Attorney, Agent, or Firm*—Dechert Price & Rhoads

[57] ABSTRACT

NO synthetase inhibitors intended to reduce the consumption of alcohol or to prevent excessive alcohol consumption in patients exhibiting an alcohol behavioral dependency are disclosed. Among the cerebral NO synthetase inhibitors, L-nitroarginine may be particularly mentioned.

22 Claims, 5 Drawing Sheets

NO SYNTHETASE INHIBITORS AS MEDICINAL PRODUCTS INTENDED TO REDUCE ALCOHOL CONSUMPTION OR TO PREVENT EXCESSIVE ALCOHOL CONSUMPTION

The present invention relates to a medicinal product intended to prevent excessive alcohol consumption.

Nitrogen monoxide (NO) is a feedback messenger produced by a number of neurons which are involved in the processes of memorization and adaptation, for example those of the hypothalamus containing vasopressin (Böhme et al. 1993).

The effect of NO synthetase (NOS) inhibitors on hypotension in patients suffering from septic shock have been studied (Petros et al. 1991 and Lefroy et al. 1993). In particular, NO synthetase inhibitors such as L-NMMA or L-NAME have been administered in man in the treatment of the hemodynamic manifestation of septic shock or of hepatic insufficiency.

Some studies have suggested that NO synthetase could play a role in the intake of food and in the subsequent weight gain (Morley and Flood 1994).

It has finally been shown that the inhibition of NO synthetase decreases the so-called phenomenon of "rapid tolerance to alcohol" (Khanna et al. 1993). In this publication, the authors studied adaptation to a test of movement coordination when this test is performed under repeated forced alcohol intoxication. In this case, the alcohol intoxication itself (given by the degree of alcoholemia) is not reduced. The same authors (Khanna et al. 1990) have moreover shown that the development of rapid or acute tolerance is not correlated with the consumption of alcohol in the same animals.

None of these publications has suggested that an NO synthetase inhibitor could have an effect on the consumption of alcohol.

It has been discovered according to the present invention that an NO synthetase inhibitor has an effect on the alcohol consumption behavior, which consumption it reduces, making it possible to decrease the deleterious effects of alcohol, especially in dependent subjects. Thus, the consumption of alcohol in rats, provoked either by "limited access" (appetence), or by "chronic intoxication by inhalation" (behavioral dependency) is prevented or reduced.

It is particularly important to observe that at doses where the NO synthetase inhibitor has no or very little effect on the total daily intake of liquid and the total daily intake of food, the consumption of alcohol is reduced both in terms of absolute quantity of alcohol and in terms of alcohol/water ratio. This shows that the effects on the consumption of liquid and food which are described in the, literature, and the effect on the consumption of alcohol according to the present invention, are different in nature.

The subject of the present invention is therefore the use of a cerebral NO synthetase inhibitor for preparing a medicinal product intended to reduce the consumption of alcohol or to prevent excessive alcohol consumption in patients exhibiting an alcohol behavioral dependency.

This medicinal product may in particular provide a therapeutic aid, especially during alcohol disintoxication cures.

Three types of NO synthetases have been described in the brain so far: two which are constitutive cytosolic and membrane-bound and one which is inducible.

Among the NO synthetase inhibitors, there may be mentioned more particularly the inhibitors of the constitutive and membrane-bound NO synthetase subtype which is linked to the N-methyl-D-aspartate (NMDA) type glutamate receptor.

The principal inhibitors of the different constitutive NO synthetases are the derivatives of L-arginine, which is the substrate of these enzymes including especially the L-NMMA, L-NA and L-NAME derivatives whose formulae are given below.

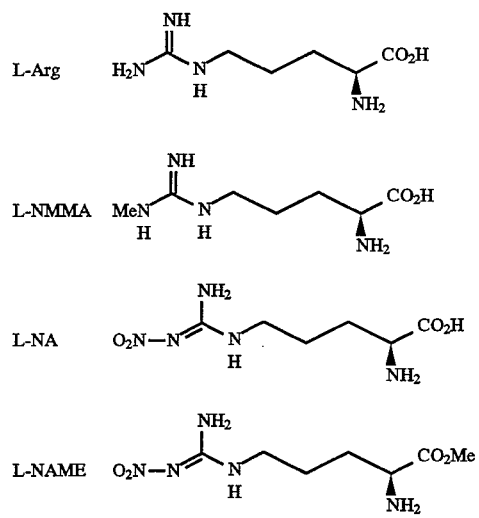

Preferably, L-NA is used as cerebral NOS inhibitor according to the present invention.

The subject of the present invention is also a composition intended to prevent or reduce alcohol consumption, which contains, as active ingredient, an NO synthetase inhibitor as mentioned above, preferably at a dose where the total daily intake of liquid and of food is not, or is only slightly, reduced, that is to say is not significantly reduced.

Other advantages and characteristics of the present invention will emerge in the light of the detailed description below.

Two procedures were used which allow a significant voluntary consumption of alcohol ad libitum (alcohol/water 10%) in male and female rats. The first procedure termed "limited access" consists in offering this free choice for only 1 hour each day; the second procedure consists in an unlimited access ad libitum after an optional period of substantial chronic intoxication by inhalation of alcohol vapor (4 weeks) (procedure termed "behavioral dependency"). In both cases, when the consumption of alcohol either per hour or per day has stabilized, a solution of n-nitroarginine (LNA), a competitive inhibitor specific for cerebral NO synthetase, is administered i.p. at the dose of 50 mg/kg of body weight, 30 minutes before the limited access or in the evening before the nocturnal period of unlimited availability ad libitum. The administration of L-NO-ARG causes the mean alcohol intake to fall by 40% (in the females) to 70% (in the males) in the two procedures. This administration produces only a slight and transient fall in the total intake of liquid and in the intake of food. The consumption of alcohol after the injection of L-NO-ARG is reduced both in terms of absolute quantity of alcohol and in terms of alcohol/water ratio (preference). The coadministration of L-arginine and L-NO-ARG shows the specificity of the alcohol consumption-reducing effect. These results show the role of NO in regulating the intake of alcohol and the possibility of using NO synthetase inhibitors in the treatment of alcoholism.

The results are presented in FIGS. 1 to 5.

Figure 1B:
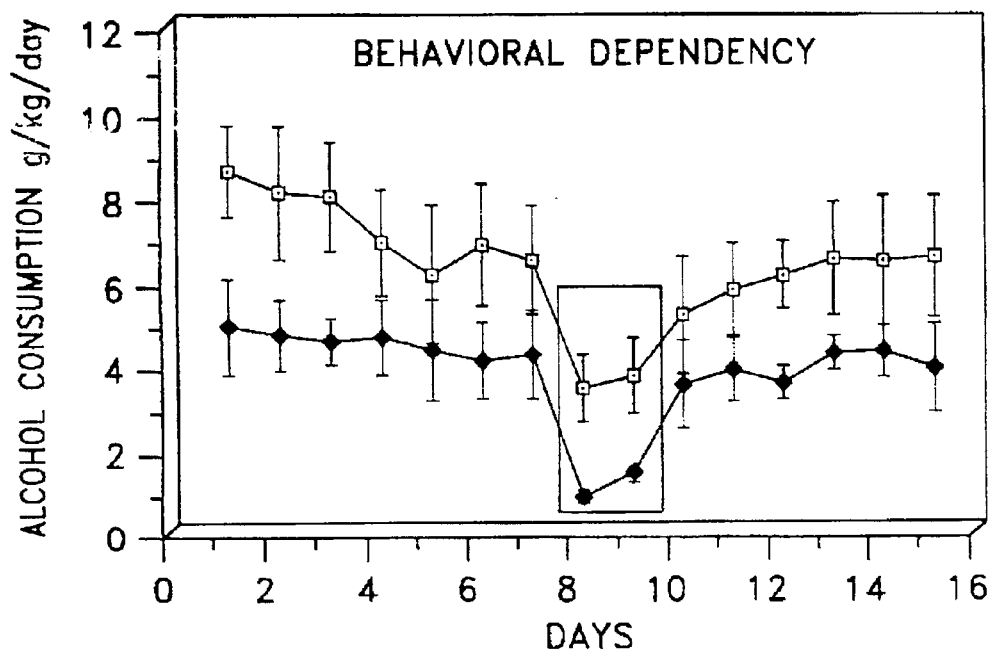

FIG. 1A and 1B represent the effect of L-nitroarginine on the consumption of alcohol according two different procedures. In both procedures—limited access (FIG. 1A) and behavioral dependency (FIG. 1B)—i.p. injections of L-NO-ARG were performed either before the limited access of one hour, or at 18 h before the nocturnal period, on two consecutive days or one week apart; often, the values obtained over these two days were averaged.

Figure 2A:
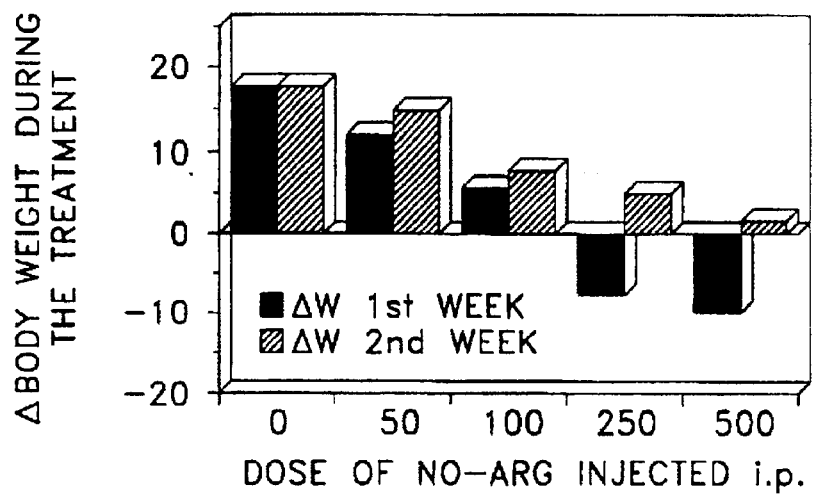
Figure 2B:
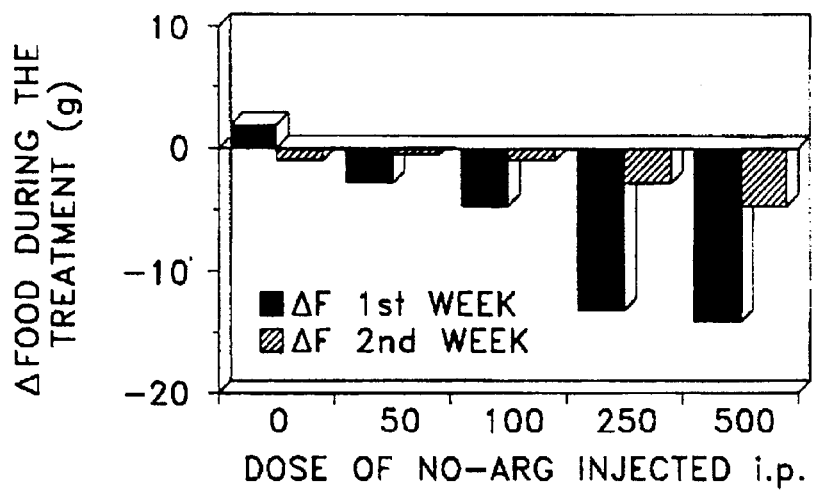
Figure 2C:
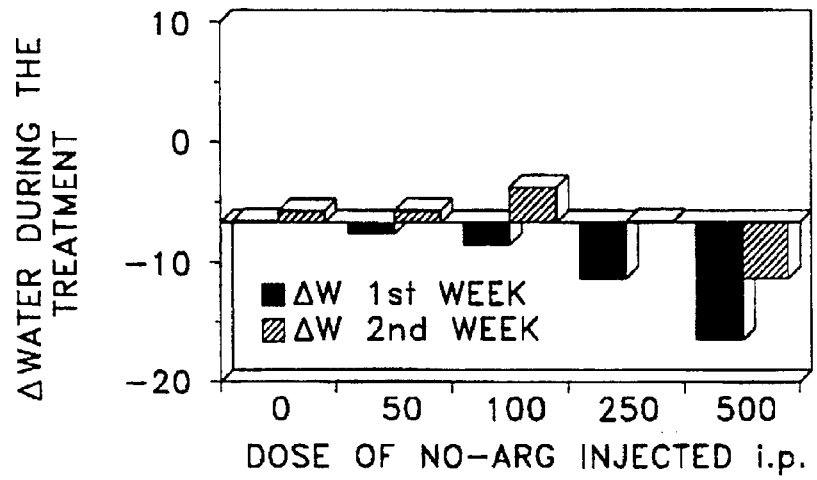

FIGS. 2A–2C present the change in weight, in the consumption of food and in the consumption of water during the two days of treatment. The possibly toxic effect of this procedure was studied by the variations in body weight (FIG. 2A), in the consumption of food (FIG. 2B) and in the consumption of water (FIG. 2C) under the same conditions at several doses of L-NO-ARG: 50, 100, 250 and 500 mg/kg. The appearance of significant decreases in the three parameters is observed only from 100 mg/kg and an improvement is noted at all doses in the 2nd week.

Figure 3A:
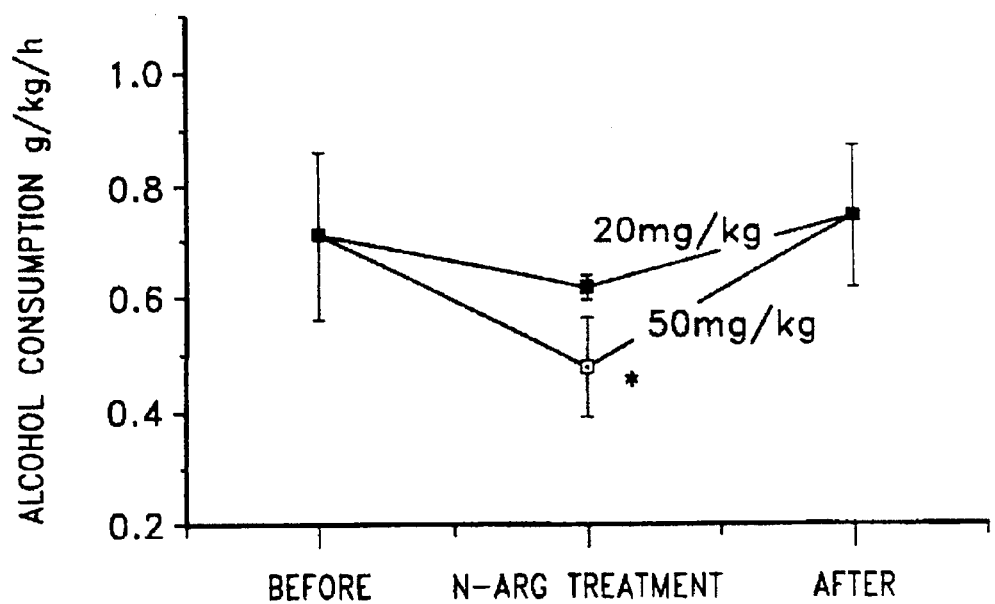
Figure 3B:
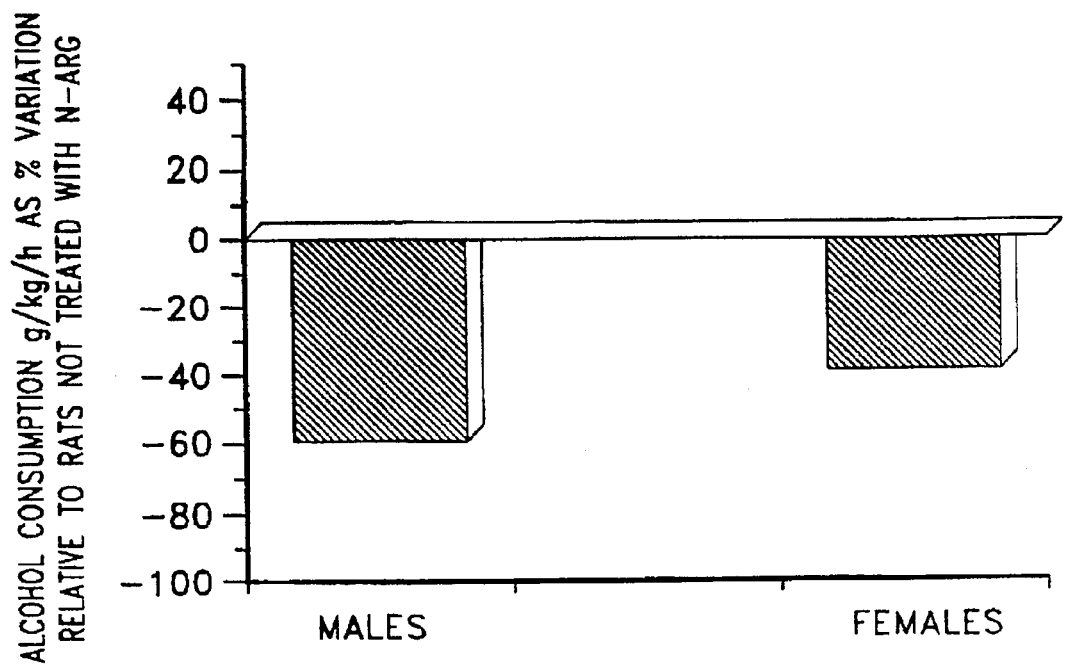

FIGS. 3A and 3B present the dose-dependent effect of L-nitroarginine on the consumption of alcohol in the limited access procedure. It was observed during the limited access procedure that the dose necessary in order to obtain a significant decrease in the consumption of alcohol by i.p. injection was 50 mg/kg and this dose was maintained in the next experiments: at 20 mg/kg j.p., a slight but statistically nonsignificant effect is observed (see FIG. 3A). On the other hand, at 50 mg i.p., the same effect becomes clearly significant (see FIG. 3B). In general, the male rats respond better than the female rats whereas they consume less alcohol (see FIG. 3B).

Figure 4:
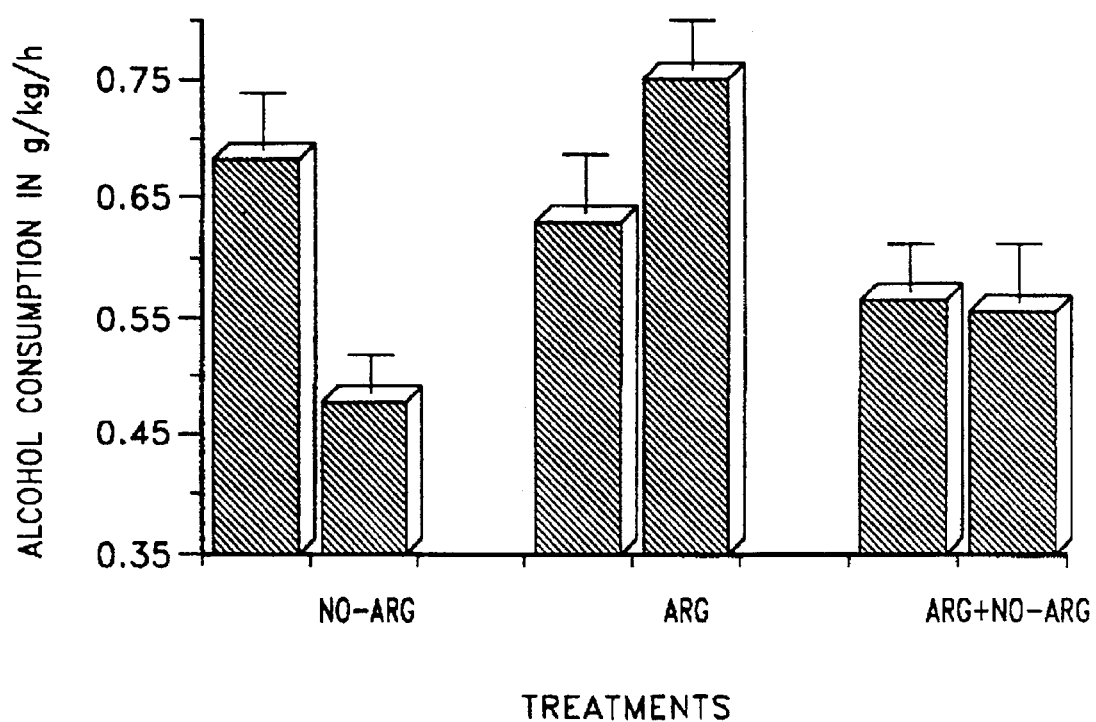

FIG. 4 presents the comparative effects of L-nitroarginine alone or coadministered with L-arginine. In the limited access procedure, the specificity of the action of L-NO-ARG was tested. L-ARG injected at more than 300 mg/kg very significantly increases the consumption of liquid but has little effect on the level of alcohol consumption; coadministered in excess at a dose of 100 mg/kg with L-NO-ARG (50 mg/kg), it completely lifts the inhibition of alcohol consumption due to this inhibitor. This result reflects competition for the L-ARG binding site and demonstrates that the production of NO is involved in the control of the alcohol consumption behavior.

Figure 5A:
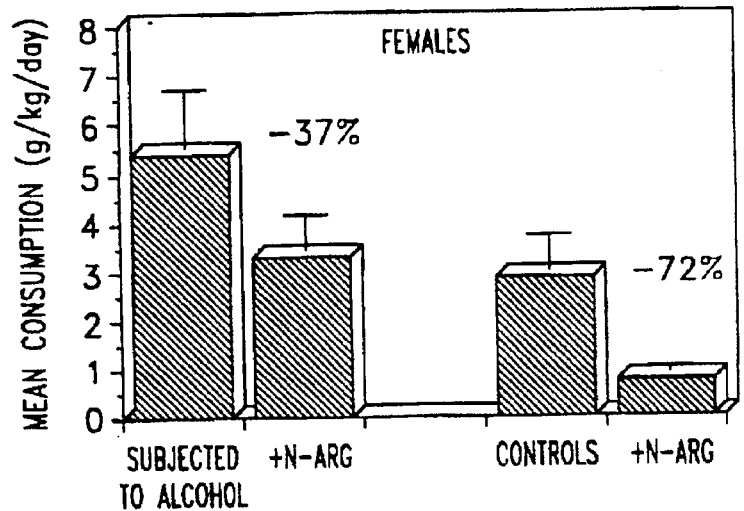
Figure 5B:
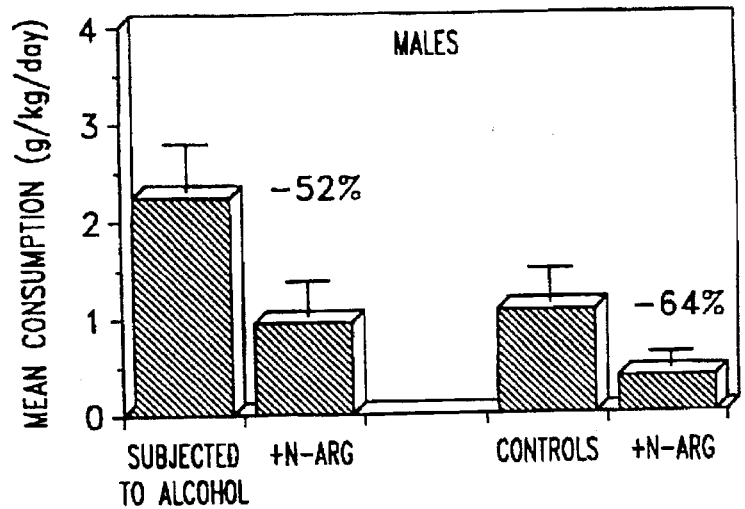
Figure 5C:
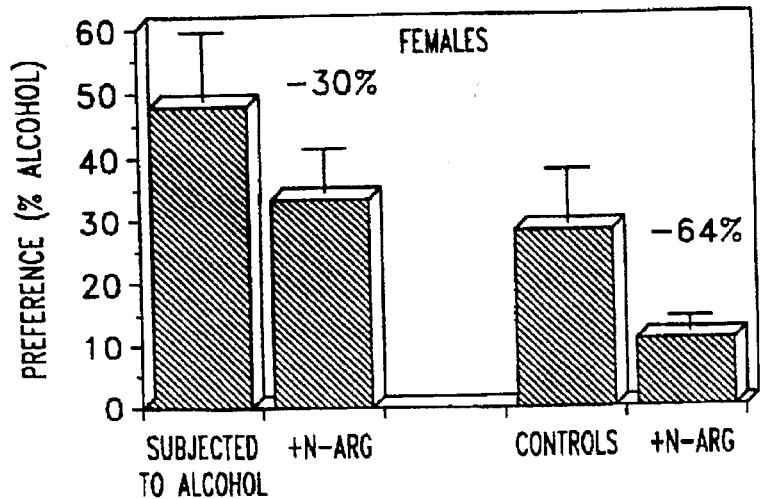

FIGS. 5A–5C present the mean daily consumption of alcohol in the behavioral dependency procedure. The situation is very similar in the behavioral dependency procedure. It should be noted that the males and the animals which were not subjected to chronic intoxication by inhalation before the access ad libitum show a greater response. Finally, the high consumptions of water over 24 hours allowed us to calculate an alcoholic solution/water preference ratio. The preference for alcohol, taking into account the small differences in the consumption of water, is greatly decreased in the animals treated with L-NO-ARG.

FIG. 5A shows mean daily consumption of alcohol for females treated with or without L-NO-ARG and with or without chronic intoxication before access ad libitum to alcohol. FIG. 5B shows mean daily consumption of alcohol for males treated with or without L-NO-ARG and with or without chronic intoxication before access ad libitum to alcohol. FIG. 5C shows the preference for alcohol for females treated with or without L-NO-ARG and with or without chronic intoxication before access ad libitum to alcohol.

BIBLIOGRAPHIC REFERENCES

1. J. E. Morley & J. F. Flood; Evidence that nitric oxide modulates food intake in mice. Life Sciences (1991) 49:707–711.

2. G. Calapai, F. Squadrito, D. Altavilla, B. Zingarelli, G. M. Campo, M. Cilia & A. P. Caputi; Evidence that nitric oxide modulates drinking behaviour. Neuropharmacology (1992) 31:761–764.

3. L. E. Lambert, J. P. Whitten, B. M. Baron, H. C. Cheng, N. S. Doherty & I. A. McDonald; Nitric oxide synthesis in the CNS, endothelium and macrophages differs in its sensitivity to inhibition by arginine analogues. Life Sciences (1991) 48:69–75.

4. M. A. Dwyer, D. S. Bredt & S. H. Snyder; Nitric oxide synthase: irreversible inhibition by n-$N^G$-Nitroarginine in brain in vitro and in vivo. Biochem. Biophys. Res. Comm. (1991) 176:1136–1141.

5. C. Hölscher a S. P. R. Rose; An inhibitor of nitric oxide synthesis prevents memory formation in the chick. Neurosc. Letters (1992) 145:165–167.

6. J. M. Khanna, G. S. Morato, G. Shah, A. Chau & H. Kalant; Inhibition of nitric oxide synthesis impairs rapid tolerance to ethanol. Brain Res. Bull. (1993) 32:43–47.

7. Y. A. Kolesnikov, C. G. Pick & G. W. Pasternak; $N^G$-Nitro-L-Arginine prevents morphine tolerance. Eur. J. Pharmacol. (1992) 221:399–400.

8. G. A. Böhme, C. Bon, M. Lemaire, M. Reibaud, O. Piot, J. M. Stutzmann, A. Doble a J. C. Blanchard, Altered synaptic plasticity and memory formation in nitric oxide synthase inhibitor-treated rats. Proc. Natl. Acad. Sci., USA (1993) 90:9191–9194.

9. J. E. Morley & J. F. Flood Effect of competitive antagonist of NO synthase on weight and food intake in obese and diabetic mice. Am. J. Physiol. (1994) 266:R164–R168.

10. P. Klatt, K. Schmidt, F. Brunner & B. Mayer Inhibitors of brain nitric oxide synthase. J. Biol. Chem. (1994) 269:1674–1680.

11. A. Petros, D. Bennett, P. Vallance Effect of nitric oxide synthase inhibitors on hypotension in patients with septic shock. Lancet (1991) 338:1557–1558.

12. D. C. Lefroy, D. Tousoulis & T. Crake Inhibition of nitric oxide synthesis. Lancet (1993) 342:1487–1488.

13. J. M. Khanna, E. Kalant, A. K. Chau & E. Sharma Initial sensitivity, acute tolerance and alcohol consumption in four inbred strains of rats. Phychopharmacology (1990) 101:390–395.

I claim:

1. A method of reducing alcohol consumption by a mammal comprising administering a NO synthetase inhibiting effective amount of a NO synthetase inhibitor.

2. The method of claim 1, wherein the NO synthetase inhibitor is administered in an amount effective to inhibit a membrane-bound synthetase subtype that is linked to a NMDA-type glutamate receptor.

3. The method of claim 1, wherein the NO synthetase inhibitor is an arginine derivative selected from the group consisting of L-NA, L-NMMA, L-NAME and mixtures thereof.

4. The method of claim 3, wherein the administered NO synthetase inhibitor is L-NA.

5. The method of claim 1, wherein humans exhibiting an alcohol behavioral dependency are treated to reduce alcohol consumption.

6. The method of claim 1, wherein the NO synthetase inhibitor is an inhibitor of a constitutive NO synthetase that is linked to a NMDA-type glutamate receptor.

7. A method of reducing alcohol consumption by a mammal comprising administering an alcohol consumption reducing effective amount of a NO synthetase inhibitor.

8. The method of claim 7, wherein the NO synthetase inhibitor is an arginine derivative selected from the group consisting of L-NA, L-NMMA, L-NAME and mixtures thereof.

9. The method of claim 8, wherein the administered NO synthetase inhibitor is L-NA.

10. The method of claim 7, wherein the amount of the NO synthetase inhibitor administered is less than the amount effective to substantially affect daily intake of liquid or food.

11. The method of claim 7, wherein humans exhibiting an alcohol behavioral dependency are treated to reduce alcohol consumption.

12. A method of reducing the consumption of alcohol without substantially affecting the daily intake of liquid or food comprising administering an alcohol consumption reducing effective amount of an NO synthetase inhibitor which is less than a daily liquid or food intake subtantially reducing effective amount of the NO synthetase inhibitor.

13. The method of claim 12, wherein the NO synthetase inhibitor is administered in an amount effective to inhibit a membrane-bound synthetase subtype that is linked to a NMDA-type glutamate receptor.

14. The method of claim 12, wherein the NO synthetase inhibitor is an arginine derivative selected from the group consisting of L-NA, L-NMMA, L-NAME and mixtures thereof.

15. The method of claim 14, wherein the administered NO synthetase inhibitor is L-NA.

16. The method of claim 10, wherein humans exhibiting an alcohol behavioral dependency are treated to reduce alcohol consumption.

17. A pharmaceutical composition for reducing alcohol consumption by a mammal comprising a NO synthetase inhibitor in an amount that is less than the amount effective to substantially affect daily intake of liquid and food, wherein the NO synthetase inhibitor is an inhibitor of a membrane-bound NO synthase linked to a NMDA receptor.

18. The pharmaceutical composition of claim 17, wherein the NO synthetase inhibitor is in an amount that is effective to reduce alcohol consumption in a mammal.

19. The composition of claim 17, wherein the NO synthetase inhibitor is an arginine derivate selected from the group consisting of L-NA, L-NMMA, L-NAME and mixtures thereof.

20. The composition of claim 19, wherein the NO synthase inhibitor is L-NA.

21. A pharmaceutical dosage form comprising the arginine derivative of claim 19 in an amount selected to deliver between 50 mg/kg/day and 100 mg/kg/day or arginine derivative to a treatment subject.

22. The composition of claim 17, wherein the NO synthetase inhibitor is an inhibitor of a constitutive NO synthetase that is linked to a NMDA-type glutamate receptor.

* * * * *